United States Patent [19]

Gross

[11] Patent Number: 4,498,899
[45] Date of Patent: Feb. 12, 1985

[54] TAMPON APPLICATOR

[75] Inventor: Richard A. Gross, Richmond, Va.

[73] Assignee: Ethyl Molded Products Company, Richmond, Va.

[21] Appl. No.: 626,582

[22] Filed: Jul. 2, 1984

Related U.S. Application Data

[63] Continuation of Ser. No. 365,830, Apr. 5, 1982, abandoned.

[51] Int. Cl.³ .............................................. A61F 15/00
[52] U.S. Cl. ..................................................... 604/16
[58] Field of Search ........................... 604/11, 14–16, 604/18, 904

[56] References Cited

U.S. PATENT DOCUMENTS

| 4,269,187 | 5/1981 | Sakurai et al. | 604/14 |
| 4,273,125 | 6/1981 | Sakurai | 604/16 |
| 4,276,881 | 7/1981 | Lilaonitkul | 604/14 |
| 4,286,595 | 9/1981 | Ring | 604/16 |
| 4,291,696 | 9/1981 | Ring | 604/16 |
| 4,329,991 | 5/1982 | Sakurai | 604/16 |

FOREIGN PATENT DOCUMENTS

| 0138491 | 5/1947 | Australia | 604/18 |
| 0269801 | 5/1965 | Australia | 604/15 |
| 0726606 | 3/1955 | United Kingdom | 604/15 |

Primary Examiner—C. Fred Rosenbaum
Assistant Examiner—Michelle N. Lester
Attorney, Agent, or Firm—Donald L. Johnson; John F. Sieberth; E. Donald Mays

[57] ABSTRACT

This invention relates to a tampon applicator having a first elongated hollow thermoplastic tube which is receivable of a tampon and a second elongated hollow thermoplastic tube which is capable of receiving within its interior the first hollow tube for packaging purposes and which is capable of being inserted into the interior of the first hollow tube for purposes of dispensing the tampon from the first hollow tube. This dual function is achievable by the utilization of an accordian wall portion for the second hollow tube which allows it to change from a diameter larger than the outside diameter of the first hollow tube to a diameter smaller than the inside diameter of the first hollow tube.

9 Claims, 7 Drawing Figures

TAMPON APPLICATOR

This application is a continuation of application Ser. No. 365,830, filed Apr. 5, 1982, now abandoned.

BACKGROUND OF THE INVENTION

Presently on the market is a tampon assembly which features a hollow tube into which the tampon is packaged. The hollow tube has an open end which receives the plunger and which is in contact with the distal end of the tampon. The plunger is depressed to urge the tampon out of the hollow tube. At the other end of the hollow tube there is a slited intergral hemispherical wall. Generally speaking the slits are four in number and are displaced approximately 90° apart. This hemispherical wall protects the proximate end of the tampon and also enables ease of insertion of the tampon within the hollow tube into the vagina. Once the hollow tube is inserted the plunger is depressed and the tampon is urged out of the hollow tube. The hemispherical wall, due to the slits and the pliable nature of the thermoplastic material of which the tube is made, will open to allow movement of the tampon completely out of the tube.

Presently this type of tampon assembly is packaged with the plunger positioned inside the hollow tube and adjacent the distal end of the tampon. The length of the assembly, therefore, equals the length of the hollow tube plus the length of the plunger portion outside of the hollow tube. It would be beneficial if this packaged length could be reduced to realize a reduction in package size. Reduction in package size results in savings in shipping costs and convenience in use for the tampon user.

Therefore it is an object of this invention to provide a tampon assembly of reduced length without loss of convenience and functionality in use.

THE INVENTION

This invention relates to a tampon applicator of reduced length. The tampon applicator of this invention comprises a first elongated hollow thermoplastic tube which has an open end and a slited hemispherical end. This first hollow tube is receivable of a tampon. The tampon applicator also has a second elongated hollow thermoplastic tube which has and accordian wall portion whereby the diameter of this second tube is changeable from a first diameter to a second diameter. The first diameter is sufficiently large to allow this second hollow tube to receive within its interior the first described hollow tube. The second diameter, however, must be sufficiently small to allow the second hollow tube to be received within the interior or the first hollow tube. When the second hollow tube is received into the interior of the first hollow tube it can function as a plunger to urge the tampon out of the first hollow tube. Generally speaking the second hollow tube will be no longer than the length of the first hollow tube.

To package the tampon applicator of this invention the first hollow tube is inserted within the second hollow tube. At this point the accordian wall portion of the second hollow tube will be in its expanded mode. When the tampon applicator is ready for use, the second hollow tube is pulled from the first hollow tube and inserted into the interior of the first hollow tube until abutment with the tampon is achieved. At this point the accordian wall portion of the second hollow tube is in a compressed mode which allows for the second hollow tube to have an outside diameter smaller than the inside diameter of the first hollow tube. In its position within the first hollow tube the second hollow tube can act as a plunger for dispensing of the tampon.

Generally speaking, it has been found desirable that the accordian wall portion traverse at least 90° as measured with the long axis of the second hollow tube as the center of the arc. A most highly perferred accordian wall portion will traverse 180°. The amount of accordian wall portion needed will of course depend upon the difference between the second hollow tube's largest diameter and its smallest diameter as required to achieve the functions described. When the second hollow tube of this invention is utilized the first hollow tubes utilized in the market place today it has been found that the accordian wall portion should traverse the beforementioned 180° arc and that there should be at least four pleats making up the accordian wall portion. A greater or smaller number of pleats may be needed in other instances depending upon the flexability of the material of construction of the second hollow tube and upon the overall dimensions of the two hollow tubes.

Since the tampon applicator of this invention can be packaged with the first hollow tube inserted into the second hollow tube and since the second hollow tube will act as a plunger, the overall packaged length of the tampon applicator is essentially equal to the length of the second hollow tube. There is no need for a plunger arm to be protruding from the rear of the first hollow tube as is the case for present day tampon applicators.

The tampon applicator of this invention can be made of any suitable thermoplastic material, with ethylene vinyl acetate copolymers, low density polyethylene and linear low density polyethylene being preferred. The main requirment for the material of construction is that it be sufficiently flexible to allow for the accordian action required of the accordian wall portion.

These and other features of this invention contributing to satisfaction in use and economy in manufacture will be more fully understood from the following description of a preferred embodiment and the accompanying drawings in which identical numerals refer to identical parts and in which.

Figure 2:
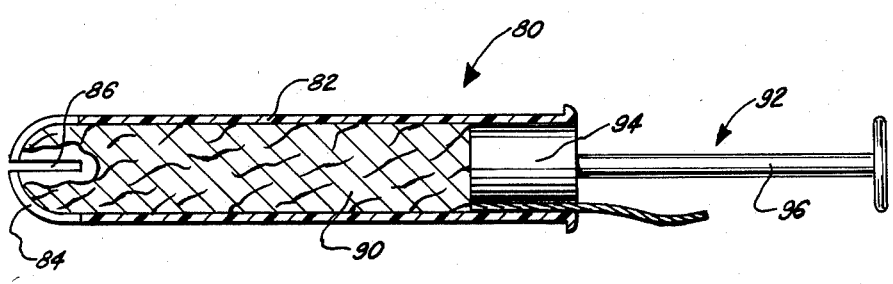
FIG. 2 is a sectional view of a prior art tampon.

Referring now to FIG. 2 there can be seen a prior art tampon applicator generally designated by the numeral 80. Tampon applicator 80 has a hollow tube 82 which receives within its interior tampon 90. Hollow tube 82 is open on one end and has at the other end a hemispherical wall 84. In hemispherical wall 84 are a plurality of slits 86. Recieved in the open end of hollow tube 82 and in abutment with tampon 90 is a plunger, generally designated by the numeral 92. Plunger 92 is made of a piston 94 and a plunger arm 96. To dispense tampon 90 from this prior art tampon applicator requires that plunger 92 be moved forward so that tampon 90 can press against hemispherical wall 84 and cause it to open thereby allowing passage of tampon 90 from hollow tube 82. As can be seen, the overall length of tampon applicator 80 comprises the length of hollow tube 82 plus the length of plunger arm 96.

The tampon applicator of this invention is shown in FIGS. 1 and 3–7. Referring to these figures it can be seen that the tampon applicator of this invention, generally designated by the numeral 10 comprises a first hollow tube, generally designated by the numeral 12 and a second hollow tube, generally designated by the numeral 20. First hollow tube 12 has a main columnar body portion 15 which has an opening 19 on one end and a hemispherical wall 14 on the other end. Hemispherical wall 14 has four slits 16 cut therein. These slits are spaced at 90° intervals of hemispherical wall 14. Tampon 40 is received within the first hollow tube 12.

Figure 5:
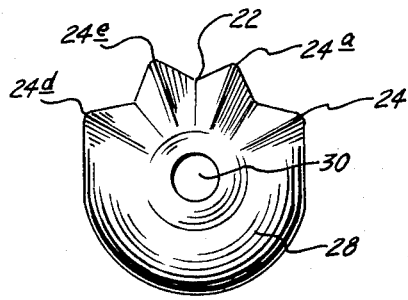
FIG. 5 is an end elevational view of the tampon applicator shown in FIG. 1.
Figure 6:
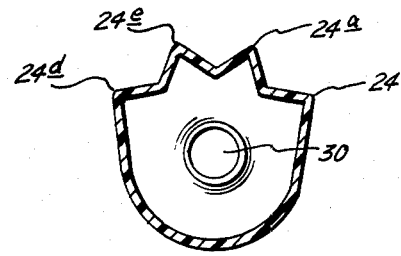
FIG. 6 is a sectional view taken through section lines 6—6 in FIG. 3.

Second hollow tube 20 has a curved body portion 26 and an accordian wall portion 22. Accordian wall portion 22 is capable of compression and expansion due to its accordian-like structure. This accordian-like structure is made up of a plurality of accordian pleats 24, 24A and 24C. As can be seen in FIGS. 5 and 6, accordian wall portion 22 traverses approximately a 180° arc as measured with the center axis of second hollow tube 20 at the arc center.

Second hollow tube 20 is open at one end and has a hemispherical wall 28 at its other end. Coaxially positioned with the long axis of second hollow tube 20 is aperture 30 which is in hemispherical wall 28.

Figure 3:
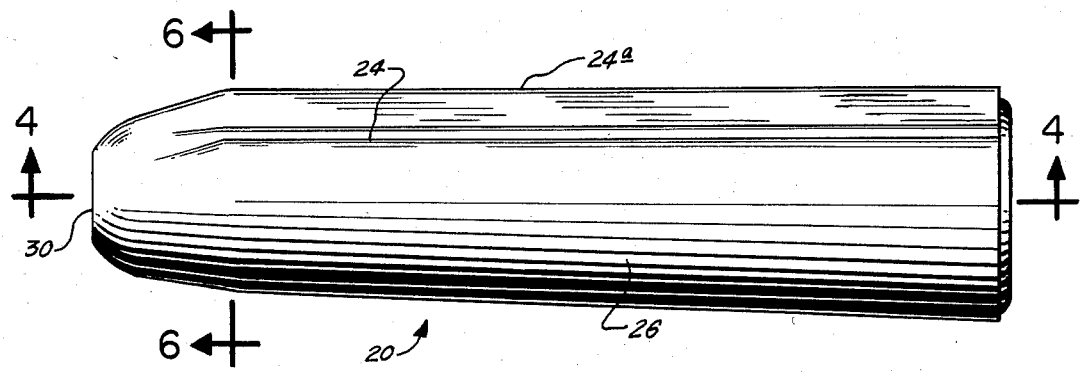
FIG. 3 is a side elevational view of the tampon applicator shown in FIG. 1.
Figure 4:
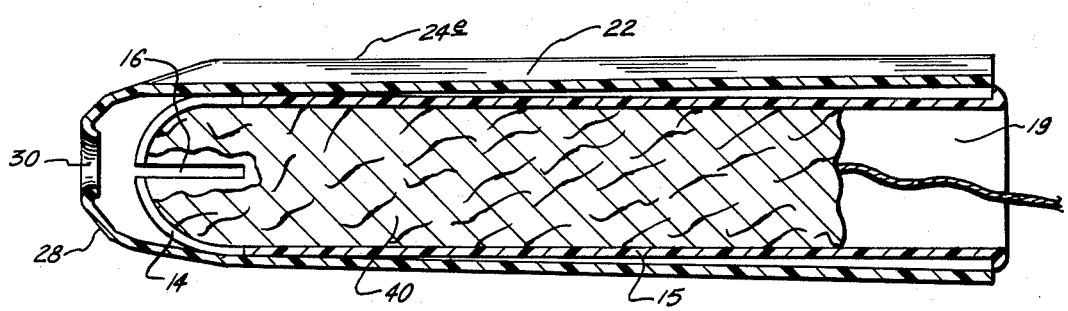
FIG. 4 is a sectional view taken through the section lines 4—4 in FIG. 3.

As can be seen in FIGS. 3 and 4 second hollow tube 20 can receive within its interior first hollow tube 15. In this mode accordian wall portion 22 will be in the expanded or relaxed position. With first hollow tube 15 in the interior of second hollow tube 20 the tampon applicator is ready for packaging. As can be appreciated the overall length of the tampon applicator as packaged will be less than the case for the before described prior art tampon applicator as no provision has to be made for the extra length caused by the protrusion of a plunger arm.

Figure 1:
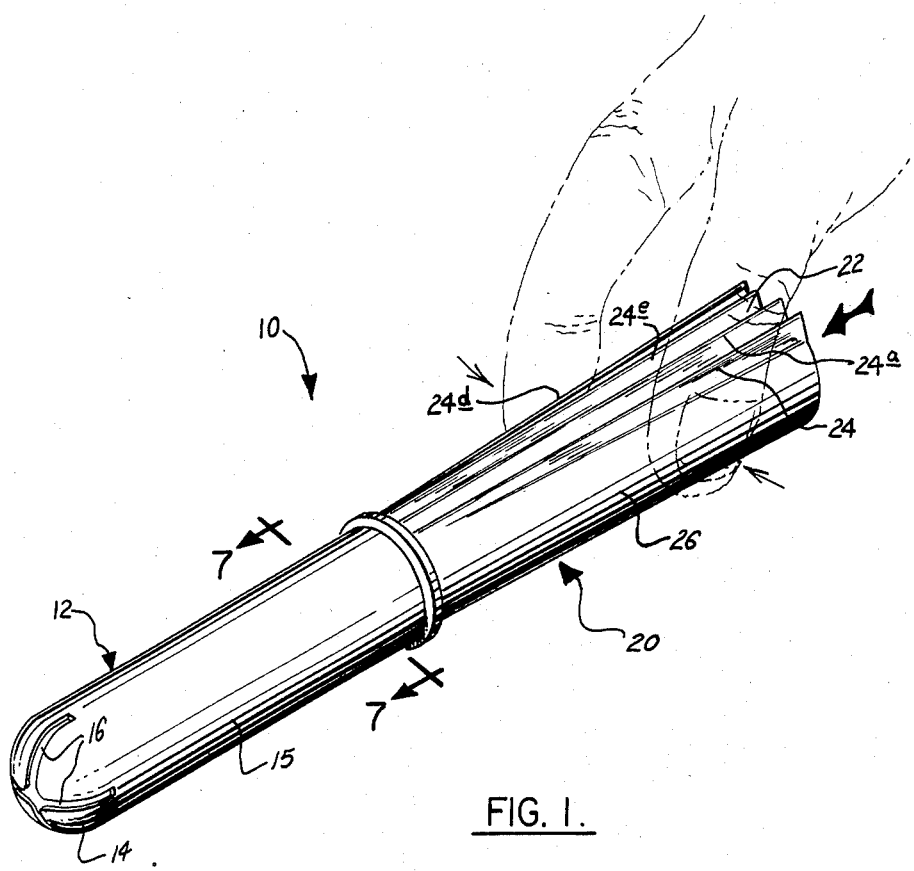
FIG. 1 is a perspective view of a tampon applicator of this invention.
Figure 7:
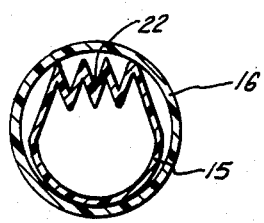
FIG. 7 is a sectional view taken through section lines 7—7 in FIG. 1.

When tampon applicator 10 is ready for use, first hollow tube 15 is removed from the interior of second hollow tube 20. Second hollow tube 20 is then inserted into the open end of first hollow tube 15. The string, which forms a part of tampon 40 can be threaded through aperture 30. Insertion of second hollow tube 20 into first hollow tube 15 will require that second hollow tube 20 take on a reduced diameter. This reduction in diameter and the resultant compression of accordian wall portion 22 is shown in FIGS. 1 and 7. With second hollow tube 20 in the interior of first hollow tube 15 and in abutment with tampon 40, second hollow tube 20 will function as a plunger so that tampon 40 can be pushed from first hollow tube 15.

Not only does the tampon applicator of this invention provide for a reduction in overall length when packaged, it also is very economical to manufacture. Both first hollow tube 15 and second hollow tube 20 can be made from simple injection molding techniques. In fact, due to the unique construction of second hollow tube 20 it may be possible to blow mold second hollow tube 20.

I claim:

1. A tampon applicator comprising:
    (A) a first elongated hollow thermoplastic tube having an open end and a slotted hemispherical other end, said first elongated hollow thermoplastic tube being receivable of a tampon; and
    (B) a second elongated hollow thermoplastic tube having an opening at its rear end to admit said first tube, a hemispherical wall at its front end, an imperforate body having a curved wall portion integrally formed with an accordian pleated wall portion made by a series of flexible, preformed, generally V-shaped grooves in a longitudinal extending portion of said body whereby the diameter of said second elongated hollow thermoplastic tube is changeable from a first diameter to a second diameter, said first diameter being sufficiently large to allow said second elongated hollow thermoplastic tube to receive within its interior said first elongated hollow thermoplastic tube, and said second diameter being sufficiently small to allow said second elongated hollow thermoplastic tube to be received in the interior of said first elongated hollow thermoplastic tube.

2. The tampon applicator of claim 1 wherein said first elongated hollow thermoplastic tube is of an ethylene vinyl acetate copolymer, low density polyethylene, or linear low density polyethylene.

3. The tampon applicator of claim 1 wherein said second elongated hollow thermoplastic tube is of an ethylene vinyl acetate copolymer, low density polyethylene, or linear low density polyethylene.

4. The tampon applicator of claim 1 wherein said accordian wall portion traverses at least 90° as measured with the long axis of said second elongated hollow thermoplastic tube at the center of the arc.

5. The tampon applicator of claim 1 wherein said accordian wall portion traverses approximately 180° as measured with the long axis of said second elongated hollow thermoplastic tube at the center of the arc.

6. The tampon applicator of claim 1 wherein said accordian wall portion has at least two pleats.

7. The tampon applicator of claim 5 wherein said accordian wall portion has at least four pleats.

8. The tampon applicator of claim 6 wherein said first elongated hollow thermoplastic tube is of an ethylene vinyl acetate copolymer, low density polyethylene, or linear low density polyethylene.

9. The tampon applicator of claim 7 wherein said second elongated hollow thermoplastic tube is of an ethylene vinyl acetate copolymer, low density polyethylene, or linear low density polyethylene.

* * * * *